(12) United States Patent
Ng et al.

(10) Patent No.: US 10,377,882 B2
(45) Date of Patent: Aug. 13, 2019

(54) POLYMER LATEX COMPOSITION FOR DIP-MOLDING APPLICATIONS

(71) Applicant: Synthomer Sdn. Bhd., Kluang (MY)

(72) Inventors: Thian Hong Ng, Batu Pahat (MY); Claudia Eigen, Dorsten (DE); Alexandra Abele, Dulmen (DE); Gareth Simpson, Cambridge (GB)

(73) Assignee: Synthomer Sdn. Bhd., Johor Darul Takzim (MY)

( * ) Notice: Subject to any disclaimer, the term of this patent is extended or adjusted under 35 U.S.C. 154(b) by 236 days.

(21) Appl. No.: 15/534,764

(22) PCT Filed: Dec. 12, 2014

(86) PCT No.: PCT/MY2014/000268
§ 371 (c)(1),
(2) Date: Jun. 9, 2017

(87) PCT Pub. No.: WO2016/093689
PCT Pub. Date: Jun. 16, 2016

(65) Prior Publication Data
US 2017/0327669 A1    Nov. 16, 2017

(51) Int. Cl.
| | | |
|---|---|---|
| C08L 9/02 | (2006.01) |
| A41D 19/00 | (2006.01) |
| C08F 236/12 | (2006.01) |
| C08L 9/04 | (2006.01) |
| C08L 13/02 | (2006.01) |
| A61B 42/00 | (2016.01) |
| A61F 6/04 | (2006.01) |
| B29C 41/14 | (2006.01) |

(52) U.S. Cl.
CPC ........... *C08L 9/04* (2013.01); *A41D 19/00* (2013.01); *A61B 42/00* (2016.02); *A61F 6/04* (2013.01); *B29C 41/14* (2013.01); *C08F 236/12* (2013.01); *C08L 9/02* (2013.01); *C08L 13/02* (2013.01); *C08F 2500/26* (2013.01)

(58) Field of Classification Search
CPC ... C08L 9/04; C08L 9/02; C08L 13/02; A61B 42/00; A41D 19/00; A61F 6/04; B29C 41/14; C08F 236/12; C08F 2500/26
USPC ........................................................ 524/565
See application file for complete search history.

(56) References Cited

U.S. PATENT DOCUMENTS

| | | |
|---|---|---|
| 2,859,193 A | 11/1958 | Kowalewski |
| 5,084,514 A | 1/1992 | Szczechura et al. |
| 5,147,907 A | 9/1992 | Rinck et al. |
| 5,290,832 A | 3/1994 | Schwerzel et al. |
| 5,358,998 A | 10/1994 | Wendel et al. |
| 5,750,618 A | 5/1998 | Vogt et al. |
| 6,040,379 A | 3/2000 | Luebke et al. |
| 6,080,813 A | 6/2000 | Wendel et al. |
| 6,759,473 B1 | 7/2004 | Nakamura et al. |
| 3,003,716 A1 | 8/2011 | Evstatieva et al. |
| 8,530,563 B2 | 9/2013 | Evstatieva et al. |
| 2006/0052513 A1 | 3/2006 | Butz et al. |
| 2009/0105424 A1 | 4/2009 | Kodama et al. |
| 2012/0149859 A1 | 6/2012 | Yang et al. |
| 2013/0062029 A1 | 3/2013 | Levin et al. |
| 2014/0182064 A1 * | 7/2014 | Song ............... C08F 251/00 8/94.33 |
| 2014/0302265 A1 * | 10/2014 | Yang ............... C08L 9/04 428/36.8 |

FOREIGN PATENT DOCUMENTS

| | | |
|---|---|---|
| CA | 2079726 A1 | 4/1993 |
| CA | 2574819 A1 | 3/2006 |
| CA | 2742885 A1 | 6/2010 |
| DE | 19540997 A1 | 5/1997 |
| EP | 0408099 A1 | 1/1991 |
| JP | 352901 A | 3/1991 |
| JP | 5209024 A | 8/1993 |
| JP | 7268169 A | 10/1995 |
| JP | 2006321954 A | 11/2006 |
| JP | 2008512526 A | 4/2008 |
| JP | 2009197149 A | 9/2009 |
| JP | 2012509971 A | 4/2012 |
| WO | 9909251 A1 | 2/1999 |
| WO | 0136553 A1 | 5/2001 |
| WO | 2009047233 A1 | 4/2009 |
| WO | 2009123637 A1 | 10/2009 |
| WO | 2011146367 A1 | 11/2011 |
| WO | 2011157679 A1 | 12/2011 |

* cited by examiner

*Primary Examiner* — Kelechi C Egwim
(74) *Attorney, Agent, or Firm* — The Webb Law Firm (57) ABSTRACT

A polymer latex composition for dip-molding applications includes the reaction product obtained by free-radical emulsion polymerization in aqueous medium of ethylenically unsaturated monomers including; (a) 19.9 to 90 wt.-% of at least one aliphatic conjugated diene; (b) 9.9 to 80 wt.-% of at least one unsaturated nitrile; (c) 0.1 to 10 wt.-% of at least one ethylenically unsaturated acid; (d) 0 to 19 wt.-% of at least one aromatic vinyl compound, and (e) 0 to 20 wt.-% of at least one further ethylenically unsaturated compound different from any of compounds (a) to (d), the weight percentages being based on the total amount of monomers, wherein the emulsion polymerization is conducted in presence of a degraded polysaccharide having a DE of 2 to 90 measured according to ISO 5377 (Dec. 15, 1981) to a method for making said polymer latex composition, to a curable polymer latex compound including said polymer latex composition, to a method for making dip molded latex films employing said curable polymer latex compound, to a film made from said polymer latex composition and to articles including said film or being coated with said polymer latex composition.

20 Claims, 2 Drawing Sheets

POLYMER LATEX COMPOSITION FOR DIP-MOLDING APPLICATIONS

CROSS-REFERENCE TO RELATED APPLICATIONS

This application is the United States national phase of International Application No. PCT/MY2014/000268 filed Dec. 12, 2014, the disclosure of which is hereby incorporated in its entirety by reference.

BACKGROUND OF THE INVENTION

Field of the Invention

The present invention relates to a polymer latex composition obtained by free-radical emulsion polymerization wherein the emulsion polymerization is conducted in presence of degraded polysaccharide that is particularly suitable for the preparation of dip-molded articles, particularly gloves. Accordingly, the present invention is also related to a method for making such a polymer latex, a compounded polymer latex composition suitable for the production of dip-molded articles, to a method for making dip-molded latex films and to latex articles comprising a latex film made from the above polymer latex composition.

Technical Considerations

Examples of polymer latex compositions that are prepared by emulsion polymerization in presence of starch or degraded starches are known.

For example EP-A 408 099 discloses a semi-continuous process for polymerizing a monomer mixture consisting of 20 to 100 wt.-% of a diene, 0 to 80 wt.-% of an aromatic vinyl monomer and 0 to 50 wt.-% of a different ethylenically unsaturated monomer in presence of a chemically modified dextrin. Although (meth)acrylonitrile might be a suitable ethylenically unsaturated monomer in the sense of EP-A 408 099, compositions comprising acrylonitrile are exemplified as consisting of 20 to 70 wt.-% of 1,3-butadiene, 30 to 80 wt.-% of styrene, 0 to 50 wt.-% of acrylonitrile and 0 to 5 wt.-% of an ethylenically unsaturated mono- or dicarboxylic acid. In that reference applicability of the obtained polymer latex composition, particularly as adhesives, additives in paint, textile and paper applications, as binders for pigmented coatings and for mineral pigments of fibre in the construction industry are mentioned, but there is no hint that the latex compositions described in EP-A 408 099 are suitable for dip-molded articles.

U.S. Pat. No. 5,358,998, WO 2011/146367, WO 2011/157679, DE 195 40 997, WO 2009/123637, WO 2009/047233 and WO 99/09251 describe polymer latex compositions that are prepared by emulsion polymerization in presence of starch or degraded starch. The latices are styrene alkyl(meth)acrylate latices or styrene butadiene latices. Although in some of these references the possibility of adding (meth)acrylonitrile as optional additional ethylenically unsaturated monomer is described, the latices described therein contain high amounts of vinyl aromatic monomers, particularly styrene. Furthermore, these latices are particularly useful as adhesives or binders for paper coating compositions. None of these references relates to dip-molded articles.

U.S. Pat. No. 6,759,473 relates to a coating composition that is coated onto a dip-molded article such as a glove in order to improve the donning properties of the dip-molded article, particularly a glove. First a glove mold is dipped in a standard vulcanizable polymer latex compound, whereby the carboxyl-modified acrylonitrile butadiene copolymer latex is prepared by emulsion polymerization of 5 parts of methacrylic acid, 28 parts of acrylonitrile and 67 parts of 1,3-butadiene. Thereafter, the dip-forming formulation applied glove mold is then dried at elevated temperature prior to dipping into a coating composition. The coating composition is prepared by emulsion polymerization of a broad range of ethylenically unsaturated monomers in presence of hydroxyl group-containing water-soluble polymers. A long list of possible hydroxyl-containing water-soluble polymers including chemically modified starch derivatives like alkyl starches, carboxymethyl starch or oxidized starch. But degraded starch is not mentioned. Furthermore, the preferred hydroxyl-containing water-soluble polymer for polymerizing the latex for the coating composition is polyvinyl alcohol as exemplified in all examples in that reference. The examples in U.S. Pat. No. 6,759,473 show improved donning properties, but the process of obtaining a glove having such improved properties is costly and complicated. Particularly, the reference discloses a two-step process wherein in the first step a standard vulcanizable polymer latex compound comprising a carboxylated acrylonitrile butadiene latex is formed to provide the supporting structure of the glove to achieve the required tensile properties such as tensile strength and elongation. Then, in a second step a coating is applied to the inside of the glove in order to improve the donning properties. Thus, two latices have to be prepared and a two-step process is necessary to obtain the gloves having improved donning and putting-off properties.

Thus, it is the object of the present invention to provide a polymer latex composition that can be used in a standard single-step process for the preparation of dip-molded articles that provides improved donning properties without compromising the tensile properties of the dip-molded article.

SUMMARY OF THE INVENTION

Surprisingly, the present inventors found that the above object can be attained by a polymer latex composition for dip-molding applications comprising the reaction product obtained by free-radical emulsion polymerization in aqueous medium of ethylenically unsaturated monomers comprising
(a) 19.9 to 90 wt.-% of at least one aliphatic conjugated diene;
(b) 9.9 to 80 wt.-% of at least one unsaturated nitrile;
(c) 0.1 to 10 wt.-% of at least one ethylenically unsaturated acid;
(d) 0 to 19 wt.-% of at least one aromatic vinyl compound, and
(e) 0 to 20 wt.-% of at least one further ethylenically unsaturated compound different from any of compounds (a) to (d),
the weight percentages being based on the total amount of monomers,
wherein the emulsion polymerization is conducted in the presence of a degraded polysaccharide having a DE of 2 to 90 measured according to ISO 5377 (Dec. 15, 1981).

In a further aspect the present invention relates to a method for making a polymer latex composition for dip-molding applications comprising subjecting unsaturated monomers comprising
(a) 19.9 to 90 wt.-% of at least one aliphatic conjugated diene;

(b) 9.9 to 80 wt.-% of at least one unsaturated nitrile;
(c) 0.1 to 10 wt.-% of at least one ethylenically unsaturated acid;
(d) 0 to 19 wt.-% of at least one aromatic vinyl compound, and
(e) 0 to 20 wt.-% of at least one further ethylenically unsaturated compound different from any of compounds (a) to (d), the weight percentages being based on the total amount of monomers, to free-radical emulsion polymerization in aqueous medium,
wherein the emulsion polymerization is conducted in the presence of a degraded polysaccharide having a DE of 2 to 90 measured according to ISO 5377 (Dec. 15, 1981).

Furthermore, the present invention is directed to a curable polymer latex compound suitable for the production of dip molded articles comprising the polymer latex composition as defined above and optionally components selected from
i) sulfur and accelerators for the sulfur vulcanization;
ii) polyvalent cations;
iii) crosslinkers; and
iv combinations thereof.

According to a further aspect the present invention is directed to a method for making dip molded latex films by
(a) immersing a mold having the desired shape of the final article in a coagulant bath comprising a solution of a metal salt;
(b) removing the mold from the bath and optionally drying the mold;
(c) immersing the mold as treated in step (a) and (b) in the above defined curable polymer latex compound;
(d) removing the mold from the latex composition and optionally immersing the latex coated mold in a water bath;
(e) optionally drying the latex coated mold;
(f) heat treating the latex coated mold obtained from step (d) or (e) at a temperature of 80 to 180° C.; and
(g) removing the latex article from the mold.

Further aspects of the present invention relate to:
a film made from the polymer latex composition of the present invention;
a latex article comprising the above latex film that are selected from surgical gloves, examination gloves, condoms, catheters and industrial and household gloves;
the use of the polymer latex composition according to the present invention for the production of dip molded articles or for coating and impregnating a substrate;
an article coated or impregnated with the polymer latex composition according to the present invention.

DETAILED DESCRIPTION OF THE PRESENT INVENTION

The present invention relates to a polymer latex composition comprising the reaction product obtainable by free-radical emulsion polymerization in an aqueous medium of the above defined ethylenically unsaturated monomers in presence of a degraded polysaccharide having a DE of 2 to 90, measured according to ISO 5377 (Dec. 15, 1981).

According to the present invention, in the emulsion polymerization process any degraded polysaccharide having the DE requirement as above can be employed. The term "polysaccharide" encompasses polysaccharides and oligosaccharides. Suitable examples are glucose syrup, commercially available from e.g Cargill Deutschland GmbH, Krefeld, Germany or Roquette, Lestrem, France and other alternatives of degraded polysaccharides that can be used according to the present invention.

The degraded polysaccharide according to the present invention has a DE of 2 to 90, measured according to ISO 5377 (Dec. 15, 1981). Preferably the DE is 38 to 80, more preferred 38 to 70, even more preferred 40 to 65 and most preferred 40 to 63. Thus the lower limit of the DE range of preferred degraded polysaccharides can be 38, 39, 40, 41, 42, 43, 44 or 45 and the upper limit of the DE range of preferred degraded polysaccharides can be 90, 85, 80, 75, 73, 71, 70, 69, 68, 67, 66, 65, 64 or 63.

The degraded polysaccharide can be applied in the free-radical emulsion polymerization process of the present invention in broad ranges. Preferably, the degraded polysaccharide of the present invention is present in an amount of 1-60 wt.-%, preferably 2-50, and more preferred 3-45 wt.-%, based on the total weight of ethylenically unsaturated monomers employed in the polymerization process.

Thus, the degraded polysaccharide according to the present invention can be present in amounts of at least 1 wt.-%, at least 3 wt.-%, at least 5 wt.-%, at least 7 wt.-%, at least 8 wt.-%, at least 10 wt.-%, at least 11 wt.-%, at least 12 wt.-%, at least 13 wt.-%, at least 14 wt.-%, at least 15 wt.-%, at least 16 wt.-%, at least 17 wt.-%, at least 18 wt.-%, at least 19 wt.-%, at least 20 wt.-%, at least 21 wt.-%, at least 22 wt.-%, at least 23 wt.-%, at least 24 wt.-%, at least 25 wt.-%, at least 26 wt.-%, at least 27 wt-%, at least 28 wt.-%, at least 29 wt.-%, at least 30 wt.-%, at least 31 wt.-%, at least 32 wt.-%, at least 33 wt.-%, at least 34 wt.-%, or at least 35 wt.-%, based on the total weight of ethylenically unsaturated monomers.

Likewise, the degraded polysaccharide according to the present invention can be used in amounts of no more than 60 wt.-%, no more than 55 wt.-%, no more than 53 wt.-%, no more than 51 wt.-%, no more than 50 wt.-%, no more than 49 wt.-%, no more than 48 wt.-%, no more than 47 wt.-%, no more than 46 wt.-%, no more than 45 wt.-%, no more than 44 wt.-%, no more than 43 wt.-%, no more than 42 wt.-%, no more than 41 wt.-%, no more than 40 wt.-%, no more than 39 wt.-%, no more than 38 wt.-%, no more than 37 wt.-%, or no more than 36 wt.-%.

A person skilled in the art will understand that any range formed by any of the explicitly disclosed lower limits and upper limits is explicitly encompassed in the present specification.

The ethylenically unsaturated monomers to be polymerized in the free-radical emulsion polymerization according to the present invention comprise:
(a) 19.9 to 90 wt.-% of at least one aliphatic conjugated diene;
(b) 9.9 to 80 wt.-% of at least one unsaturated nitrile;
(c) 0.1 to 10 wt.-% of at least one ethylenically unsaturated acid;
(d) 0 to 19 wt.-% of at least one aromatic vinyl compound, and (e) 0 to 20 wt.-% of at least one further ethylenically unsaturated compound different from any of compounds (a) to (d), the weight percentages being based on the total amount of monomers.

Conjugated diene monomers suitable for the preparation of the latices according to the present invention include conjugated diene monomers, selected from 1,3-butadiene, isoprene and 2,3-dimethyl-1,3-butadiene. 1,3-butadiene is the preferred conjugated diene according to the present invention. Typically the amount of conjugated diene monomer ranges from 19.9 to 90 wt.-%, preferably from 25 to 85 wt.-%, more preferred from 30 to 75 wt.-%, most preferred from 40 to 70 wt.-%, based on the total weight of monomers. Thus, the conjugated diene may be present in amounts of at least 20 wt.-%, at least 22, wt.-%, at least 24 wt.-%, at least 26 wt.-%, at least 28 wt.-%, at least 30 wt.-%, at least 32 wt.-%, at least 34 wt.-%, at least 36 wt.-%, at least 38 wt.-%, or at least 40 wt.-%, based on the total weight of the ethylenically unsaturated monomers.

Accordingly, the conjugated diene monomers can be used in amounts of no more than 90 wt.-%, no more than 85 wt.-%, no more than 80 wt.-%, no more than 78 wt.-%, no more than 76 wt.-%, no more than 74 wt.-%, no more than 72 wt.-%, no more than 70 wt.-%, no more than 68 wt.-%, no more than 66 wt.-%, no more than 64 wt.-%, no more than 62 wt.-%, no more than 60 wt.-%, no more than 58 wt.-%, or no more than 56 wt.-%.

A person skilled in the art will appreciate that any range between any of the explicitly disclosed lower and upper limit is herein disclosed.

Unsaturated nitrile monomers which can be used in the present invention include polymerizable unsaturated aliphatic nitrile monomers which contain from 2 to 4 carbon atoms in a linear or branched arrangement, which may be substituted either by acetyl or additional nitrile groups. Such nitrile monomers include acrylonitrile, methacrylonitrile and fumaronitrile, with acrylonitrile being most preferred. These nitrile monomers can be included in amounts from 9.9 to 90 wt.-%, preferably from 10 to 70 wt.-%, and more preferred from 15 to 50 wt.-%, even more preferred from 20 to 50 wt.-%, most preferred from 23 to 43 wt.-%, based on the total weight of ethylenically unsaturated monomers.

Thus, the unsaturated nitrile may be present in amounts of at least 12 wt.-%, at least 14 wt.-%, at least 16 wt.-%, at least 18 wt.-%, at least 20 wt.-%, at least 22 wt.-%, at least 24 wt.-%, at least 26 wt.-%, at least 28 wt.-%, at least 30 wt.-%, at least 32 wt.-%, at least 34 wt.-%, at least 36 wt.-%, at least 38 wt.-%, or at least 40 wt.-%, based on the total weight of the ethylenically unsaturated monomers.

Accordingly, the unsaturated nitrile monomers can be used in amounts of no more than 80 wt.-%, no more than 75 wt.-%, no more than 73 wt.-%, no more than 70 wt.-%, no more than 68 wt.-%, no more than 66 wt.-%, no more than 64 wt.-%, no more than 62 wt.-%, no more than 60 wt.-%, no more than 58 wt.-%, no more than 56 wt.-%, no more than 54 wt.-%, no more than 52 wt.-%, no more than 50 wt.-%, no more than 48 wt.-%, no more than 46 wt.-%, or no more than 44 wt.-%. A person skilled in the art will appreciate that any range between any of the explicitly disclosed lower and upper limit is herein disclosed.

The ethylenically unsaturated carboxylic acid monomers suitable for use in the present invention include monocarboxylic acid and dicarboxylic acid monomers and monoesters of dicarboxylic acid. Carrying out the present invention it is preferable to use ethylenically unsaturated aliphatic mono- or dicarboxylic acids or anhydrides which contain from 3 to 5 carbon atoms. Examples of monocarboxylic acid monomers include acrylic acid, methacrylic acid, crotonic acid and examples of dicarboxylic acid monomers include fumaric acid, itaconic acid, maleic acid and maleic anhydride. Examples of other suitable ethylenically unsaturated acids include vinyl acetic acid, vinyl lactic acid, vinyl sulfonic acid, 2-Methyl-2-propene-1-sulfonic acid, styrene sulfonic acid, acrylamidomethyl propane sulfonic acid and the salts thereof.

The use of ethylenically unsaturated acid monomers influences the properties of the polymer dispersion and of the coating produced thereof. The type and the amount of these monomers are determined thereby. Typically, such an amount is from 0.1 to 10 wt.-%, preferably from 0.1 to 9 wt.-%, more preferred from 0.1 to 8 wt.-%, even more preferred from 1 to 7 wt.-%, most preferred 2 to 7 wt.-%, based on the total weight of the ethylenically unsaturated monomers. Thus, the ethylenically unsaturated acid monomers may be present in amounts of at least 0.1 wt.-%, at least 0.3 wt.-%, at least 0.5 wt.-%, at least 0.7 wt.-%, at least 0.9 wt.-%, at least 1 wt.-%, at least 1.2 wt.-%, at least 1.4 wt.-%, at least 1.6 wt.-%, at least 1.8 wt.-%, at least 2 wt.-%, at least 2.5 wt.-%, or at least 3 wt.-%. Likewise, the ethylenically unsaturated acid monomers may be present in amounts of no more than 10 wt.-%, no more than 9.5 wt.-%, no more than 9 wt.-%, no more than 8.5 wt.-%, no more than 8 wt.-%, no more than 7.5 wt.-%, no more than 7 wt.-%, no more than 6.5 wt.-%, no more than 6 wt.-%, no more than 5.5 wt.-%, or no more than 5 wt.-%, based on the total weight of ethylenically unsaturated monomers. A person skilled in the art will appreciate that any range defined by an explicitly disclosed lower limit and an explicitly disclosed upper limit is disclosed herewith.

Representatives of vinyl-aromatic monomers include, for example, styrene, α-methylstyrene, p-methylstyrene, t-butylstyrene and vinyltoluene. It is also possible to use divinyl aromatic compounds such as divinylbenzene. Mixtures of one or more of the vinyl-aromatic compounds may also be used. The preferred monomers are styrene and α-methylstyrene. The vinyl-aromatic compounds can be used in a range of from 0 to 19 wt.-%, preferably from 0 to 15 wt.-%, more preferred from 0 to 10 wt.-%, and most preferred from 0 to 7 wt.-%, based on the total weight of ethylenically unsaturated monomers. Thus, the vinyl-aromatic compound can be present in an amount of no more than 18 wt.-%, no more than 16 wt.-%, no more than 14 wt.-%, no more than 12 wt.-%, no more than 10 wt.-%, no more than 8 wt.-%, no more than 6 wt.-%, no more than 4 wt.-%, no more than 2 wt.-%, or no more than 1 wt.-%, based on the total weight of ethylenically unsaturated monomers. Vinyl-aromatic compounds may also be completely absent.

Optionally, the ethylenically unsaturated monomer used in the free-radical emulsion polymerization to form the polymer latex according to the present invention may include additional ethylenically unsaturated monomers that are different from the above-defined monomers a) to d). These monomers may be selected from esters of (meth)acrylic acid, vinyl esters, and amides of ethylenically unsaturated acids or ethylenically unsaturated silane compounds.

Vinyl ester monomers which can be used according to the present invention include vinyl acetate, vinyl proprionate, vinyl butyrate, vinyl benzoate, vinyl-2-ethylhexanoate, vinyl stearate, and the vinyl esters of versatic acid. The most preferred vinyl ester monomers for use in the present invention is vinyl acetate. Typically, the vinyl ester monomers can be present in an amount of no more than 18 wt.-%, no more than 16 wt.-%, no more than 14 wt.-%, no more than 12 wt.-%, no more than 10 wt.-%, no more than 8 wt.-%, no more than 6 wt.-%, no more than 4 wt.-%, no more than 2 wt.-%, or no more than 1 wt.-%, based on the total weight of ethylenically unsaturated monomers.

Examples of suitable ethylenically unsaturated silane compounds can be selected from triethoxy(vinyl)silane and 3-methacryloxypropyltrimethoxysilane Esters of (meth)acrylic acid that can be used according to the present invention include n-alkyl esters, iso-alkyl esters or tert-alkyl esters of acrylic or (meth)acrylic acid in which the alkyl group has from 1 to 20 carbon atoms, the reaction product of methacrylic acid with glycidyl ester of a neoacid such as versatic acid, neodecanoic acid or pivalic acid and hydroxyalkyl(meth)acrylate and alkoxyalkyl(meth)acrylate monomers.

In general, the preferred alkyl esters of (meth)acrylic acids may be selected from $C_1$-$C_{10}$ alkyl(meth)acrylate, preferably $C_1$-$C_{10}$-alkyl(meth)acrylates. Examples of such acrylate monomers include n-butyl acrylate, secondary butyl acrylate, ethyl acrylate, hexyl acrylate, tert-butyl acrylate, 2-ethyl-hexyl acrylate, isooctyl acrylate, 4-methyl-2-pentyl acrylate, 2-methylbutyl acrylate, methyl methacrylate, butyl methacrylate, n-butyl methacrylate, isobutyl methacrylate, ethyl methacrylate, isopropyl methacrylate, hexyl methacrylate, cyclohexyl methacrylate and cetyl methacrylate. Typically, the of alkyl(meth)acrylate monomers can be present in an amount of no more than 18 wt.-%, no more than 16 wt.-%, no more than 14 wt.-%, no more than 12 wt.-%, no more than 10 wt.-%, no more than 8 wt.-%, no more than 6 wt.-%, no more than 4 wt.-%, no more than 2 wt.-%, or no more than 1 wt.-%, based on the total weight of ethylenically unsaturated monomers.

The hydroxy alkyl(meth)acrylate monomers which can be used to prepare the polymer latex according to the present invention include hydroxyalkyl acrylate and methacrylate monomers which are based on ethylene oxide, propylene oxide and higher alkylene oxides or mixtures thereof. Examples are hydroxyethyl acrylate, hydroxypropyl acrylate, hydroxyethyl methacrylate, hydroxypropyl methacrylate and hydroxybutyl acrylate. Typically, hydroxy alkyl (meth)acrylate monomers can be present in an amount of no more than 18 wt.-%, no more than 16 wt.-%, no more than 14 wt.-%, no more than 12 wt.-%, no more than 10 wt.-%, no more than 8 wt.-%, no more than 6 wt.-%, no more than 4 wt.-%, no more than 2 wt.-%, or no more than 1 wt.-%, based on the total weight of ethylenically unsaturated monomers.

Alkoxyalkyl(meth)acrylate monomers which can be used in the present invention include methoxyethyl methacrylate, ethoxyethyl methacrylate, methoxyethyl methacrylate, ethoxyethyl acrylate, butoxyethyl methacrylate, methoxybutyl acrylate and methoxyethoxyethyl acrylate. Preferred alkoxyalkyl(meth)acrylate monomers are ethoxyethyl acrylate and methoxyethyl acrylate. Typically, the amount of alkoxyethyl alkyl(meth)acrylate monomers can be present in an amount of no more than 18 wt.-%, no more than 16 wt.-%, no more than 14 wt.-%, no more than 12 wt.-%, no more than 10 wt.-%, no more than 8 wt.-%, no more than 6 wt.-%, no more than 4 wt.-%, no more than 2 wt.-%, or no more than 1 wt.-%, based on the total weight of ethylenically unsaturated monomers.

Amides of ethylenically unsaturated acids that can be used for the preparation of the polymer latex according to the present invention include acrylamide, methacrylamide, and diacetone acrylamide. The preferred amide monomer is acrylamide. In order to introduce functional groups that are capable of self-crosslinking upon heat treatment into the polymer particles of the present invention monomers comprising N-methylol amide groups may be employed. Suitable monomers are N-methylol (meth)acrylamide, N-methoxymethyl-(meth)acrylamide, N-n-butoxy-methyl-(meth)acrylamide, N-iso-butoxy-methyl-(meth)acrylamide, N-acetoxymethyl-(meth)acrylamide, N(-2,2-dimethoxy-1-hydroxyethyl) acrylamide. Typically, amides of ethylenically unsaturated acid can be present in an amount of no more than 18 wt.-%, no more than 16 wt.-%, no more than 14 wt.-%, no more than 12 wt.-%, no more than 10 wt.-%, no more than 8 wt.-%, no more than 6 wt.-%, no more than 4 wt.-%, no more than 2 wt.-%, or no more than 1 wt.-%, based on the total weight of ethylenically unsaturated monomers.

According to the present invention the ethylenically unsaturated monomers to be polymerized in the free-radical emulsion polymerization may comprise:

(a) 19.9 to 90 wt.-% of isoprene;
(b) 9.9 to 80 wt.-% of acrylonitrile;
(c) 0.1 to 10 wt.-% of at least one ethylenically unsaturated acid;
(d) 0 to 19 wt.-% of at least one aromatic vinyl compound, and
(e) 0 to 20 wt.-% of at least one further ethylenically unsaturated compound different from any of compounds (a) to (d). The ranges for component (a) and/or (b) may be selected from the ranges for (a) conjugated dienes and (b) unsaturated nitrile as disclosed above. Likewise specific embodiments and amounts for the components (c), (d) and/or (e) may be selected from those as described above for components (c), (d) and (e).

In general, the polymer latex composition of the present invention can be prepared by polymerization processes which are known in the technical area, and in particular by the known latex emulsion polymerization processes, including a latex polymerization carried out with external seeds (seed latex) and a latex polymerization not carried out with seed latex or with a seed latex prepared in situ of the polymerization process. A preferred process is described in U.S. Pat. No. 5,750,618. Such process can be adapted for the polymerization of the monomers described above and the presence of the degraded polysaccharide. The method for introducing the monomers and other ingredients, such as polymerization assistants, is not particularly critical. The polymerization is then carried out under conventional conditions until the desired conversion of monomer in to polymer has been reached. Crosslinking agents and the well known adjuvants for latex polymerization, such as initiators, surfactants, bases, buffers and emulsifiers, can be used depending on requirements.

It is also possible in the polymerization process of the present invention to use a seed latex in order to adjust the desired particle size. The seed suitable according to the invention consists of, for example, latices based on the latices to be produced according to the present invention. But it is also possible to use a seed latex that is totally different from the latex according to the present invention, as long as the desired particle size is obtained. The particle size of the initially introduced seed latex is preferably in the range from 10-80 nm, even more preferred in the range from 20-50 nm.

Inorganic pigments whose particles can act as seeds for the subsequent polymerization can also be used as seed in the process according to the invention. Pigments having an average particle size of 5-100 nm, such as silica sole, are for example suitable.

The quantity of the seed to be used depends on the size of the latex to be produced and is usually 0.01-5 weight percent, preferably 0.1-3 weight percent, based on the total amount of monomers used in the polymerization process.

The process for the preparation of the above-described polymer latex can be performed at temperatures of from 0 to 130° C., preferably of from 0 to 100° C., particularly preferably of from 5 to 70° C., very particularly preferably of from 5 to 60° C., in the presence of no or one or more emulsifiers and one or more initiators. The temperature includes all values and sub-values there between, especially including 5, 10, 15, 20, 25, 30, 35, 40, 45, 50, 55, 60, 65, 70, 75, 80, 85, 90, 95, 100, 105, 110, 115, 120 and 125° C.

Initiators which can be used when carrying out the present invention include water-soluble and/or oil-soluble initiators which are effective for the purposes of the polymerization. Representative initiators are well known in the technical area and include, for example: azo compounds (such as, for example, AIBN, AMBN and cyanovaleric acid) and inorganic peroxy compounds, such as hydrogen peroxide, sodium, potassium and ammonium peroxydisulfate, peroxycarbonates and peroxyborates, as well as organic peroxy compounds, such as alkyl hydroperoxides, dialkyl peroxides, acyl hydroperoxides, and diacyl peroxides, as well as esters, such as tertiary butyl perbenzoate and combinations of inorganic and organic initiators.

The initiator is used in a sufficient amount to initiate the polymerization reaction at a desired rate. In general, an amount of initiator of from 0.01 to 5, preferably of from 0.1 to 4%, by weight, based on the weight of the total polymer, is sufficient. The amount of initiator is most preferably of from 0.01 to 2% by weight, based on the total weight of the polymer. The amount of initiator includes all values and subvalues there between, especially including 0.01, 0.1, 0.5, 1, 1.5, 2, 2.5, 3, 4 and 4.5% by weight, based on the total weight of the polymer.

The above mentioned inorganic and organic peroxy compounds may also be used alone in combination with one or more suitable reducing agents as is well known in the art. Examples of such reducing agents which may be mentioned are sulfur dioxide, alkali metal disulfites, alkali metal and ammonium hydrogen sulfites, thiosulfates, dithionites and formaldehyde sulfoxylates, as well as hydroxylamine hydrochloride, hydrazine sulfate, iron (II) sulfate, cuprous naphthanate, glucose, sulfonic acid compounds such as sodium methane sulfonate, amine compounds such as dimethylaniline and ascorbic acid. The quantity of the reducing agent is preferably 0.03 to 10 parts by weight per part by weight of the polymerization initiator.

Surfactants or emulsifiers which are suitable for stabilizing the latex particles include those conventional surface-active agents for polymerization processes. The surfactant or surfactants can be added to the aqueous phase and/or the monomer phase. An effective amount of surfactant in a seed process is the amount which was chosen for supporting the stabilization of the particle as a colloid, the minimization of contact between the particles and the prevention of coagulation. In a non-seeded process, an effective amount of surfactant is the amount which was chosen for influencing the particle size.

Representative surfactants include saturated and ethylenically unsaturated sulfonic acids or salts thereof, including, for example, unsaturated hydrocarbonsulfonic acid, such as vinylsulfonic acid, allylsulfonic acid and methallylsulfonic acid, and salts thereof; aromatic hydrocarbon acids, such as, for example, p-styrenesulfonic acid, isopropenylbenzenesulfonic acid and vinyloxybenzenesulfonic acid and salts thereof; sulfoalkyl esters of acrylic acid and methacrylic acid, such as, for example, sulfoethyl methacrylate and sulfopropyl methacrylate and salts thereof, and 2-acrylamido-2-methylpropanesulfonic acid and salts thereof; alkylated diphenyl oxide disulfonates, sodium dodecylbenzenesulfonates and dihexyl esters of sodium sulfosuccinate, ethoxylated alkylphenols and ethoxylated alcohols; fatty alcohol (poly)ethersulfates.

The type and the amount of the surfactant is governed typically by the number of particles, their size and their composition. Typically, the surfactant is used in amounts of from 0 to 20, preferably from 0 to 10, more preferably from 0 to 5, parts by weight, based on the total weight of the monomers. The amount of surfactant includes all values and sub-values there between, especially including 0, 0.1, 0.5, 1, 2, 3, 4, 5, 6, 7, 8, 9, 10, 11, 12, 13, 14, 15, 16, 17, 18 and 19 parts by weight based on the total weight of the monomer. According to one embodiment of the present invention the polymerization is conducted without using surfactants.

Various protective colloids can also be used instead of or in addition to the surfactants described above. Suitable colloids include polyhydroxy compounds, such as partially acetylated polyvinyl alcohol, casein, hydroxyethyl starch, carboxymethylcellulose, hydroxyethylcellulose, hydroxypropylcellulose, polyethylene glycol and gum arabic. The preferred protective colloids are carboxymethylcellulose, hydroxyethylcellulose and hydroxypropylcellulose. In general, these protective colloids are used in contents of from 0 to 10, preferably from 0 to 5, more preferably from 0 to 2, parts by weight, based on the total weight of the monomers. The amount of protective colloids includes all values and subvalues therebetween, especially including 1, 2, 3, 4, 5, 6, 7, 8 and 9 parts by weight, based on the total weight of the monomers.

The person skilled in the art will appreciate the type and amounts of monomers bearing polar functional groups, surfactants and protective colloids are to be selected to make the polymer latex according to the present invention suitable for dip-molding applications. Thus, it is preferred that the polymer latex composition of the present invention has a certain maximum electrolyte stability determined as critical coagulation concentration of less than 30 mmol/l $CaCl_2$, preferably less than 25 mmol/l, more preferred less than 20 mmol/l, most preferred less than 10 mmol/l (determined for a total solids content of the composition of 0.1% at pH 10 and 23° C.).

If the electrolyte stability is too high then it is difficult to coagulate the polymer latex in a dip-molding process with the result that either no continuous film of the polymer latex on the immersed mold is formed or the thickness of the resulting product is non-uniform.

It is within the routine of the person skilled in the art to appropriately adjust the electrolyte stability of a polymer latex. The electrolyte stability will depend on certain different factors, for example, amount and selection of monomers to be used for making the polymer latex, especially monomers containing polar-functional groups, as well as the selection and amount of the stabilizing system, for example, the emulsion polymerization process for making the polymer latex. The stabilizing system may contain surface-active agents and/or protective colloids.

A person skilled in the art is able, depending on the selected monomers and their relative amounts for making the polymer latex of the present invention, to adjust the stabilizing system in order to achieve an electrolyte stability according to the present invention.

Since there are so many different influences on the electrolyte stability the adjustment is best made by trial and error experiments. But this can be easily done without any inappropriate effort using the test method for electrolyte stability, as disclosed above.

Furthermore the working examples below provide examples how the appropriate electrolyte stability of the polymer latex of the present invention can be adjusted. It is frequently advisable to perform the emulsion polymerization additionally in the presence of buffer substances and chelating agents. Suitable substances are, for example, alkali metal phosphates and pyrophosphates (buffer substances) and the alkali metal salts of ethylenediaminetetraacetic acid (EDTA) or hydroxyl-2-ethylenediaminetriacetic acid (HEEDTA) as chelating agents. The quantity of buffer substances and chelating agents is usually 0.001-1 weight percent, based on the total quantity of monomers.

Furthermore, it may be advantageous to use chain transfer agents (regulators) in emulsion polymerization. Typical agents are, for example, organic sulfur compounds, such as thioesters, 2-mercaptoethanol, 3-mercaptopropionic acid and $C_1$-$C_{12}$ alkyl mercaptans, n-dodecylmercaptan and t-dodecylmercaptan being preferred. The quantity of chain transfer agents, if present, is usually 0.05-3.0 weight percent, preferably 0.2-2.0 weight percent, based on the total weight of the used monomers.

Various other additives and ingredients can be added in order to prepare the latex composition of the present invention. Such additives include, for example: antifoams, wetting agents, thickeners, plasticizers, fillers, pigments, dispersants, optical brighteners, crosslinking agents, accelerators, antioxidants, biocides and metal chelating agents. Known antifoams include silicone oils and acetylene glycols. Customary known wetting agents include alkylphenol ethoxylates, alkali metal dialkylsulfosuccinates, acetylene glycols and alkali metal alkylsulfate. Typical thickeners include polyacrylates, polyacrylamides, xanthan gums, modified celluloses or particulate thickeners, such as silicas and clays. Typical plasticizers include mineral oil, liquid polybutenes, liquid polyacrylates and lanolin. Zinc oxide is a suitable crosslinking agent. Titanium dioxide ($TiO_2$), calcium carbonate and clay are the fillers typically used. Known accelerators and secondary accelerators include dithiocarbamates like zinc diethyl dithiocarbamate, zinc-dibutyl dithiocarbamate, zinc dibenyl dithiocarbamate, zinc pentamethylen dithiocarbamate (ZPD), xanthates, thiurams like tetramethylthiuram monosulfide (TMTM), Tetramethylthiuram disulfide (TMTD), tetraethylthiuram disulfide (TETD), dipentamethylenethiuram hexasulfide (DPTT), and amines, such as diphenylguanidine (DPG), di-o-tolylguanidine (DOTG), o-tolylbiguanidine (OTBG). Furthermore it can be beneficial to introduce partial neutralization to the polymerization process to regulate the ongoing degradation of the polysaccharide. A person skilled in the art will appreciate that by appropriate selections of this parameter the necessary control can be achieved.

The polymer latex of the present invention is particularly suitable for dip-molding processes. Therefore, according to one aspect of the present invention the polymer latex is compounded to produce a curable polymer latex compound that can be directly used in dip-coating processes. To get reproducible good physical film properties, it is advisable to adjust the pH of the compounded polymer latex composition by pH modifiers to be in the range of pH 7 to 11, preferably 8 to 10, more preferred 9 to 10. The compounded polymer latex composition contains the polymer latex of the present invention optionally the pH modifiers, preferably ammonia or alkali hydroxides and usual additives to be used in these compositions selected from antioxidants, pigments, $TiO_2$, fillers and dispersing agents.

It is possible to add to the polymer latex compound according to the present invention to be used in dip-molding processes conventional vulcanization systems, such as sulfur in combination with accelerators, such as thiurams and carbamates and zinc oxide to make it curable. Alternatively or additionally a crosslinker component, like for example, polyvalent cations or other polyfunctional organic compounds suitable to react with functional groups on the latex particles in order to achieve chemical crosslinking may be added. If the polymer latex of the present invention bears sufficient amounts of self-crosslinking groups as described above sulfur vulcanization systems and/or cross-linkers may be totally avoided, but the polymer latex compound of the present invention is still curable to provide dip molded articles having the required tensile properties.

In the method for making dip-molded latex articles according to the present invention first a mold having the desired shape of the final article is immersed in a coagulant bath comprising a solution of a metal salt. The coagulant is usually used as a solution in water, an alcohol or a mixture thereof. As specific examples of the coagulant the metal salts can be metal halides like calcium chloride, magnesium chloride, barium chloride, zinc chloride and aluminum chloride; metal nitrates such as calcium nitrate, barium nitrate and zinc nitrate; metal sulfates like calcium sulfate, magnesium sulfate, and aluminum sulfate; and acetic acid salts such as calcium acetate, barium acetate and zinc acetate. Most preferred are calcium chloride and calcium nitrate. The coagulant solution might contain additives to improve the wetting behavior of the former Thereafter the mold is removed from the bath and optionally dried. The such treated mold is then immersed in the compounded latex composition according to the present invention. Thereby a thin film of latex is coagulated on the surface of the mold. Alternatively it is also possible to obtain the latex film by a plurality of dipping steps, particularly two dipping steps in sequence.

Thereafter the mold is removed from the latex composition and optionally immersed in a water bath in order to extract, for example, polar components from the composition and to wash the coagulated latex film.

Thereafter the latex coated mold is optionally dried at temperature below 80° C.

Finally the latex coated mold is heat treated at a temperature of 80-180° C. in order to obtain the desired mechanical properties for the final film product. Then the final latex film is removed from the mold. The duration of the heat treatment will depend on the temperature and is typically between 1 and 60 minutes. The higher the temperature the shorter is the required treatment time.

The final heat treated polymer latex film has a tensile strength of at least about 7 MPa and an elongation at break of at least about 300%, preferably a tensile strength of at least about 10 MPa, an elongation at break of at least about 350%, more preferred a tensile strength of at least about 15 MPa and an elongation at break of at least about 400% and even more preferred a tensile strength of at least about 20 MPa and an elongation at break of at least about 500%. These mechanical properties were measured according to ASTM D412.

This process can be used for any latex article that can be produced by a dip-molding process known in the art.

The present invention is especially applicable for dip-molded latex articles selected from health care devices, like surgical gloves, examination gloves, condoms, catheters or all different kinds of industrial and household gloves.

The present invention will be further illustrated with reference to the following examples.

EXAMPLES

Example 1 (Comparative)

1.5 parts by weight (based on polymer solids) of a seed latex (average particle size 36 nm) having a solids content of 31 wt.-% and 84 parts by weight of water (based on 100 parts by weight monomer including the seed latex) were added to a nitrogen-purged autoclave and subsequently heated to 30° C. Then 0.05 parts by weight of sodium dodecyl benzene sulfonate, 0.05 parts by weight of tetra sodium ethylendiamine tetraacetate ($Na_4EDTA$), 0.05 parts by weight of sodium formaldehyde sulfoxylate, 0.005 parts by weight of ferrous sulfate and 0.08 parts by weight of cumene hydroperoxide (CHP) were added.

Then the monomers were added together with the t-dodecylmercaptane (tDDM) over a period of 5 hours (30 parts by weight acrylonitrile, 63.5 parts by weight butadiene, 5 parts by weight methacrylic acid diluted with 10 parts by weight water and 0.5 pts tDDM).

Over a period of 10 hours 2.0 parts by weight of sodium dodecyl benzene sulfonate and 0.2 parts by weight of tetra sodium pyrophosphate and 22 parts by weight water were added. The co-activator feed of 0.13 parts by weight sodium formaldehyde sulfoxylate in 8 parts by weight water was added over 14 h, a post activation of 0.04 parts by weight of t-butyl hydroperoxide in 2 parts by weight water was injected after 10 hour.

The polymerization was continued until a conversion of 98% was reached, resulting in a total solid content of 45%. The polymerization was short stopped by addition of 0.2 parts by weight of a 5% aqueous solution of diethylhydroxylamine. The pH was adjusted by ammonia to pH 7.5 and the residual monomers were removed by vacuum distillation at 60° C.:

Example 2

Example 1 was repeated with the exception that 1.5 parts by weight (based on polymer solids) of a seed latex (average particle size 36 nm) having a solids content of 31 wt.-%, 90.5 parts by weight of water (based on 100 parts by weight monomer including the seed latex) and 5 parts by weight of a degraded starch having a DE of 60 were added to a nitrogen-purged autoclave and subsequently heated to 30° C.

Example 3

Example 1 was repeated with the exception that 1.5 parts by weight (based on polymer solids) of a seed latex (average particle size 36 nm) having a solids content of 31 wt.-%, 97 parts by weight of water (based on 100 parts by weight monomer including the seed latex) and 10 parts by weight of a degraded starch having a DE of 60 were added to a nitrogen-purged autoclave and subsequently heated to 30° C.

Example 4

Example 1 was repeated with the exception that 1.5 parts by weight (based on polymer solids) of a seed latex (average particle size 36 nm) having a solids content of 31 wt.-%, 108.5 parts by weight of water (based on 100 parts by weight monomer including the seed latex) and 20 parts by weight of a degraded starch having a DE of 60 were added to a nitrogen-purged autoclave and subsequently heated to 30° C.

Example 5

Example 1 was repeated with the exception that 1.5 parts by weight (based on polymer solids) of a seed latex (average particle size 36 nm) having a solids content of 31 wt.-%, 121 parts by weight of water (based on 100 parts by weight monomer including the seed latex) and 30 parts by weight of a degraded starch having a DE of 60 were added to a nitrogen-purged autoclave and subsequently heated to 30° C.

The electrolyte stability of the polymer latex composition of examples 1 to 5 is determined as critical coagulation concentration (ccc) for a total solids content of the latex of 0.1% at pH 10 and 23° C. Under these conditions the latex is titrated with a 2.0 mol/l solution of calcium chloride (adjusted to pH 10) and the turbidity of 113 the latex was followed by photometric measurement using a Mettler Photorode DP550 as a function of calcium chloride concentration. The ccc is taken from the inflection point of the turbidity/electrolyte concentration curve. For all examples 1 to 5 the critical coagulation concentration was 8 mmol/l $CaCl_2$.

Example 6: Film Preparation (Dipped Films) and Measuring of the Dipped Films The raw latex of examples 1 to 5 was compounded and diluted to a total solid content of 18% with water. The pH was adjusted to 10.0 with a 5% potassium hydroxide solution. Dipping was conducted using a mold dipping machine. As mold a glove mold with textured fingers and smooth palm was used. The mold was heated to 55-60° C. and then dipped into a coagulant solution (18 wt.-% aqueous solution of calcium nitrate at 60° C.) for 1 second. The mold was then dried in the oven. Subsequently the heated mold (60° C.) was dipped into the compounded latex for 5 seconds, air dried for 1 minute and finally leached in water for 1 minute at 60° C. After leaching, the gloves cuff was beaded manually. The mold was then dried in the oven at 90° C. for 10 minutes followed by curing at 120° C. for 20 minutes. Finally the cured gloves were manually stripped from the mold. The side of the glove that was in contact with the mold constitutes the outer surface when the gloves is worn by a user and is referred to in the following as "working surface". The side of the glove opposite to the surface that was in contact with the mold constitutes the inner surface when the gloves is worn by a user and is referred to in the following as "donning surface", contact with the mold constitutes the inner surface when the gloves is worn by a user and is referred to in the following as "donning surface".

The gloves prepared from the latices of examples 1 to 5 were tested for tensile properties and friction properties. The results are reported in table 1.

The tensile properties of the vulcanized gloves as reported in table 1 were tested according to ASTM D412 test procedure. 6 mm dumbbell specimens were cut from gloves prepared from each latex compound; the un-aged samples were conditioned at 23±2° C. and 50±5% relative humidity for at least 24 hours prior to testing on the Hounsfield HK10KS Tensiometer fitted with H500LC extensometer.

Figure 3:
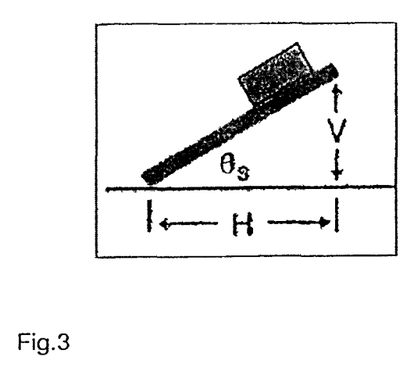
FIG. 3 is a side view of the static friction testing device as described in Example 6.

The friction properties were tested as follows:

The coefficient of friction at selected glove areas was determined. The measurement was done by using a Static friction testing device, a block gauge (125 g±0.1) and an angle level. From the dipped gloves samples were cut at defined areas: palm (Side 1), palm (Side 2), finger (Index), and finger (Thumb) (see FIG. 1). The specific testing area-working or donning area were defined. The test pieces were attached to the block gauge in a way that surface of the samples to be tested (working surface or donning surface) is outside and forms the contact surface of the samples with the sliding surface of the testing device. The friction platform was set to 0° using angle level. Then the platform was moved upwards until the block gauge started sliding down the sliding surface of the testing device. The movement was stopped, the angle was determined and the coefficient of friction was calculated according to the following equation:

$$\text{Coefficient of friction} = \mu = \tan\theta = \sin\theta(V)/\cos\theta(H)$$

Where θ=angle of friction
See FIG. 3

In table 1 the angle of friction and the coefficient of friction of the working surface and donning surface of the samples from the different selected areas of the glove are given for the gloves made from the lattices of examples 1 to 5.

TABLE 1

Glove properties

| latex composition | Ex. 6a* Example 1 | | Ex. 6b Example 2 | | Ex. 6c Example 3 | | Ex. 6d Example 4 | | Ex. 6e Example 5 | |
|---|---|---|---|---|---|---|---|---|---|---|
| amount of polysaccharide DE = 60 [wt.-%] | 0 | | 5 | | 10 | | 20 | | 30 | |
| tensile strength [MPa] | 33,2 | | 35,2 | | 31,1 | | 29,7 | | 27,6 | |
| elongation [%] | 633 | | 604 | | 642 | | 606 | | 579 | |
| working surface | θ | μ | θ | μ | θ | μ | θ | μ | θ | μ |
| Palm 1 | 47 | 1.072 | 45 | 1.000 | 46 | 1.036 | 48 | 1.111 | 40 | 0.839 |
| Palm 2 | 46 | 1.036 | 46 | 1.036 | 47 | 1.072 | 45 | 1.000 | 36 | 0.727 |
| Index | 46 | 1.036 | 46 | 1.036 | 47 | 1.072 | 42 | 0.900 | 40 | 0.839 |
| Thumb | 48 | 1.111 | 47 | 1.072 | 35 | 0.700 | 43 | 0.933 | 40 | 0.839 |
| donning surface | θ | μ | θ | μ | θ | μ | θ | μ | θ | μ |
| Palm 1 | 45 | 1.000 | 34 | 0.675 | 36 | 0.727 | 30 | 0.577 | 20 | 0.363 |
| Palm 2 | 44 | 0.966 | 36 | 0.727 | 29 | 0.554 | 27 | 0.510 | 19 | 0.344 |
| Index | 50 | 1.192 | 30 | 0.577 | 32 | 0.625 | 20 | 0.364 | 18 | 0.325 |
| Thumb | 48 | 1.111 | 36 | 0.727 | 26 | 0.488 | 22 | 0.404 | 22 | 0.404 |

*comparative

Figure 1:
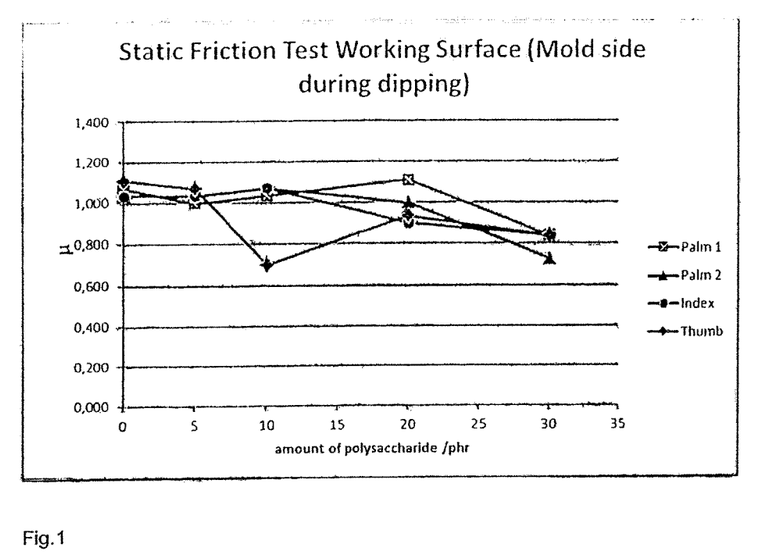
FIG. 1 is a graph of the coefficient of friction of the working surface vs. amount of degraded starch as described in Example 6.
Figure 2:
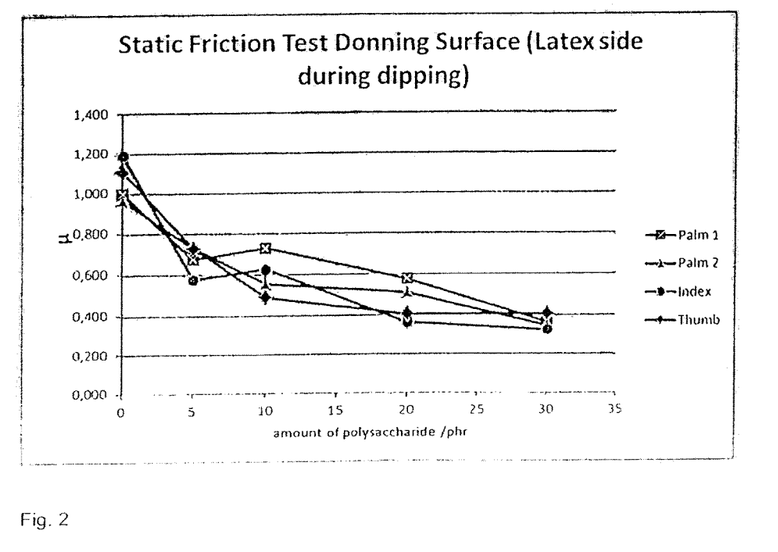
FIG. 2 is a graph of the coefficient of friction of the donning surface vs. amount of degraded starch as described in Example 6.

FIG. 1 and FIG. 2 show a graphical representation of the coefficient of friction of the working surface and donning surface respectively depending on the amount of degraded starch employed in the preparation of the latex. Surprisingly the amount of starch has only little effect on the coefficient of friction of the working surface so that the grip of the working surface is not substantially changed, whereas already a small amount of degraded starch considerably reduces the friction of the donning surface so that the glove can be more easily stripped off after use. Moreover, the tensile properties of the glove are not compromised by adding degraded starch. Thus the latex of the present invention lead to dip molding products such as gloves that have improved donning properties without compromising other desired mechanical properties in a standard dip molding process without the necessity of an additional coating step.

The invention claimed is:

1. A polymer latex composition for dip-molding applications comprising the reaction product obtained by free-radical emulsion polymerization in aqueous medium of ethylenically unsaturated monomers comprising
   (a) 19.9 to 90 wt.-% of at least one aliphatic conjugated diene;
   (b) 9.9 to 80 wt.-% of at least one unsaturated nitrile;
   (c) 0.1 to 10 wt.-% of at least one ethylenically unsaturated acid;
   (d) 0 to 19 wt.-% of at least one aromatic vinyl compound, and
   (e) 0 to 20 wt.-% of at least one further ethylenically unsaturated compound different from any of compounds (a) to (d),
   the weight percentages being based on the total amount of monomers,
   wherein the emulsion polymerization is conducted in presence of a degraded polysaccharide having a DE of 2 to 90 measured according to ISO 5377(Dec. 15, 1981).

2. The polymer latex composition of claim 1, wherein the ethylenically unsaturated monomers comprise:
   (a) 25 to 85 wt.-% of at least one aliphatic conjugated diene;
   (b) 10 to 70 wt.-% of at least one unsaturated nitrile;
   (c) 0.1 to 9 wt.-% of at least one ethylenically unsaturated acid;
   (d) 0 to 15 wt.-% of at least one aromatic vinyl compound, and
   (e) 0 to 20 wt.-% of at least one further ethylenically unsaturated compound different from any of compounds (a) to (d),
   the weight percentages being based on the total amount of monomers.

3. The polymer latex composition of claim 1, wherein the ethylenically unsaturated monomers comprise:
   (a) 30 to 75 wt.-% of at least one aliphatic conjugated diene;
   (b) 15 to 50 wt.-% of at least one unsaturated nitrile;
   (c) 0.1 to 8 wt.-% of at least one ethylenically unsaturated acid;
   (d) 0 to 10 wt.-% of at least one aromatic vinyl compound, and
   (e) 0 to 20 wt.-% of at least one further ethylenically unsaturated compound different from any of compounds (a) to (d),
   the weight percentages being based on the total amount of monomers.

4. The polymer latex composition of claim 1, wherein the ethylenically unsaturated monomers comprise:
   (a) 35 to 70 wt.-% of at least one aliphatic conjugated diene;
   (b) 20 to 50 wt.-% of at least one unsaturated nitrile;
   (c) 2 to 7 wt.-% of at least one ethylenically unsaturated acid;
   (d) 0 to 10 wt.-% of at least one aromatic vinyl compound, and
   (e) 0 to 20 wt.-% of at least one further ethylenically unsaturated compound different from any of compounds (a) to (d),
   the weight percentages being based on the total amount of monomers.

5. The polymer latex composition of claim 1, wherein the ethylenically unsaturated monomers comprise:
   (a) 40 to 65 wt.-% of at least one aliphatic conjugated diene;
   (b) 25 to 40 wt.-% of; at least one unsaturated nitrile (c) 2 to 7 wt.-% of at least one ethylenically unsaturated acid;
(d) 0 to 10 wt.-% of at least one aromatic vinyl compound, and
(e) 0 to 20 wt.-% of at least one further ethylenically unsaturated compound different from any of compounds (a) to (d),
the weight percentages being based on the total amount of monomers.

6. The polymer latex composition of claim 1, wherein at least one of:
   (a) the conjugated diene is selected from the group consisting of 1,3-butadiene, 2,3-dimethyl-1,3-butadiene and isoprene;
   (b) the at least one unsaturated nitrile is selected from the group consisting of acrylonitrile and methacrylonitrile;
   (c) the ethylenically unsaturated acid is selected from the group consisting of at least one of (meth)acrylic acid, itaconic acid, maleic acid, fumaric acid, crotonic acid, vinyl acetic acid, vinyl lactic acid, vinyl sulfonic acid, styrene sulfonic acid, acrylamidomethyl propane sulfonic acid;
   (d) the vinyl aromatic compound is selected from the group consisting of at least one of styrene, α-methyl styrene, p methylstyrene, t-butylstyrene, and vinyltoluene;
   (e) the ethylenically unsaturated monomer different from the monomers a) to d) is selected from at least one of esters of (meth)acrylic acid, vinyl esters of carboxylic acids, amides of ethylenically unsaturated acids, vinyl compounds containing sulphonate, sulphonic acid amide and/or N-methylolamide groups.

7. The polymer latex composition of claim 1, wherein
   (a) the conjugated diene is 1,3-butadiene;
   (b) the at least one unsaturated nitrile is acrylonitrile;
   (c) the ethylenically unsaturated acid is (meth)acrylic acid; and
   (d) the vinyl aromatic compound is styrene.

8. The polymer latex composition of claim 1, wherein
   (a) the conjugated diene is isoprene;
   (b) the at least one unsaturated nitrile is acrylonitrile;
   (c) the ethylenically unsaturated acid is (meth)acrylic acid; and
   (d) the vinyl aromatic compound is styrene.

9. The polymer latex composition of claim 1, wherein the degraded polysaccharide has a DE of 38 to 80.

10. The polymer latex composition of claim 1, wherein the degraded polysaccharide is present in an amount of 1-60 wt.-% based on the total weight of monomers.

11. The polymer latex composition of claim 1, having an electrolyte stability determined as critical coagulation concentration of less than 30 mmol/l $CaCl_2$ determined for a total solids content of the composition of 0.1% at pH 10 and 23° C.

12. A curable polymer latex compound for the production of dip molded articles comprising the polymer latex composition of claim 1 and optionally at least one component selected from the group consisting of
   i) sulfur and accelerators for the sulfur vulcanization;
   ii) polyvalent cations;
   iii) crosslinkers; and
   iv combinations thereof.

13. A film made from a polymer latex composition of claim 1.

14. A latex article comprising a latex film according to claim 13 being selected from the group consisting of surgical gloves, examination gloves, condoms, catheters and industrial and household gloves.

15. Article coated or impregnated with the polymer latex composition according to claim 1.

16. Article according to claim 15 comprising a coated or impregnated textile material.

17. A method for making dip molded latex films comprising
   (a) immersing a mold having the desired shape of the final article in a coagulant bath comprising a solution of a metal salt;
   (b) removing the mold from the bath and optionally drying the mold;
   (c) immersing the mold as treated in step (a) and (b) in the curable polymer latex compound of claim 16;
   (d) removing the mold from the latex composition and optionally immersing the latex coated mold in a water bath;
   (e) optionally drying the latex coated mold;
   (f) heat treating the latex coated mold obtained from step (d) or (e) at a temperature of 80 to 180° C.; and
   (g) removing the latex article from the mold.

18. A method for making a polymer latex composition for dip-molding applications comprising subjecting unsaturated monomers comprising
   (a) 19.9 to 90 wt.-% of at least one aliphatic conjugated diene;
   (b) 9.9 to 80 wt.-% of at least one unsaturated nitrile;
   (c) 0.1 to 10 wt.-% of at least one ethylenically unsaturated acid;
   (d) 0 to 19 wt.-% of at least one aromatic vinyl compound, and
   (e) 0 to 20 wt.-% of at least one further ethylenically unsaturated compound different from any of compounds (a) to (d),
   the weight percentages being based on the total amount of monomers, to free-radical emulsion polymerization in aqueous medium,
   wherein the emulsion polymerization is conducted in presence of a degraded polysaccharide having a DE of 2 to 90 measured according to ISO 5377 (Dec. 15, 1981).

19. The method of claim 18, wherein the emulsion polymerization is conducted in presence of a stabilizing system comprising surfactants, protective colloids or combinations thereof in amounts to provide an electrolyte stability determined as critical coagulation concentration of less than 30 mmol/l $CaCl_2$ determined for a total solids content of the composition of 0.1% at pH 10.

20. The method of claim 18, wherein the monomers are polymerized in presence of a seed latex for adjusting the particle size.

* * * * *

UNITED STATES PATENT AND TRADEMARK OFFICE
CERTIFICATE OF CORRECTION

PATENT NO. : 10,377,882 B2
APPLICATION NO. : 15/534764
DATED : August 13, 2019
INVENTOR(S) : Thian Hong Ng et al.

It is certified that error appears in the above-identified patent and that said Letters Patent is hereby corrected as shown below:

In the Claims

Column 16, Line 67, Claim 5, delete "of; of" and insert -- of --

Column 16, Line 67, Claim 5, delete "nitrile" and insert -- nitrile; --

Column 18, Line 2, Claim 12, delete "iv" and insert -- iv) --

Column 18, Line 22, Claim 17, delete "claim 16" and insert -- claim 12 --

Signed and Sealed this
Seventh Day of September, 2021

Drew Hirshfeld
*Performing the Functions and Duties of the*
*Under Secretary of Commerce for Intellectual Property and*
*Director of the United States Patent and Trademark Office*